(12) United States Patent
Tanbakuchi et al.

(10) Patent No.: US 7,532,015 B2
(45) Date of Patent: May 12, 2009

(54) MICROWAVE SPECTROSCOPY PROBE

(75) Inventors: Hassan Tanbakuchi, Santa Rosa, CA (US); Matthew R. Richter, Santa Rosa, CA (US); Michael B. Whitener, Santa Rosa, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/304,170

(22) Filed: Dec. 14, 2005

(65) Prior Publication Data

US 2007/0132460 A1   Jun. 14, 2007

(51) Int. Cl.
*G01R 27/04* (2006.01)
*G01R 31/02* (2006.01)

(52) U.S. Cl. ..................... 324/636; 324/72.5
(58) Field of Classification Search ............... 324/636
See application file for complete search history.

(56) References Cited

U.S. PATENT DOCUMENTS

| | | | |
|---|---|---|---|
| 3,906,270 A * | 9/1975 | Gallagher et al. ........... 313/157 |
| 4,866,371 A * | 9/1989 | De ............................. 324/639 |
| 5,025,222 A | 6/1991 | Scott et al. | |
| 5,140,377 A * | 8/1992 | Lewis et al. ................. 399/335 |
| 5,341,100 A | 8/1994 | Taylor | |
| 5,675,259 A | 10/1997 | Arndt et al. | |
| 6,127,026 A * | 10/2000 | Bonk et al. ................... 428/213 |
| 6,297,533 B1 * | 10/2001 | Mkhitarian ................... 257/336 |
| 6,319,316 B1 * | 11/2001 | Gibson et al. .................. 118/50 |
| 6,376,258 B2 | 4/2002 | Hefti | |
| 6,485,905 B2 | 11/2002 | Hefti | |
| 6,630,833 B2 | 10/2003 | Scott | |
| 6,801,029 B2 | 10/2004 | van der Weide et al. | |
| 6,831,470 B2 | 12/2004 | Xie et al. | |
| 6,870,448 B2 | 3/2005 | Whitener et al. | |
| 6,992,550 B2 * | 1/2006 | Rawnick et al. .............. 333/263 |
| 7,141,978 B2 * | 11/2006 | Peck et al. .................... 324/321 |
| 2003/0072549 A1 * | 4/2003 | Facer et al. ................... 385/129 |
| 2006/0081883 A1 * | 4/2006 | Zhang .......................... 257/208 |

FOREIGN PATENT DOCUMENTS

| WO | 02 086475 | 10/2002 |
|---|---|---|
| WO | 03 016887 | 2/2003 |
| WO | 2006 070852 | 7/2006 |

OTHER PUBLICATIONS

GB Search Report dated Apr. 19, 2007.

* cited by examiner

*Primary Examiner*—Timothy J Dole
*Assistant Examiner*—Jeff Natalini

(57) ABSTRACT

A microwave spectroscopy probe has a center conductor between a first ground plane and a second ground plane. A dielectric member has fluid channel between the center conductor and the first ground plane.

14 Claims, 3 Drawing Sheets

US 7,532,015 B2

MICROWAVE SPECTROSCOPY PROBE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

Microwave dielectric spectroscopy is a technique that uses a microwave signal to measure properties of a dielectric material. When the microwave signal is applied to the dielectric material it creates an electromagnetic field that propagates through the dielectric material. Dielectric properties of a material are determined by the material's molecular structure, and properties of the material can be deduced by observing the propagation of an electric field through it. Dielectric spectroscopy is an attractive way to evaluate a material because it can provide a real-time indication of the material's properties and is non-destructive. Dielectric spectroscopy is used in a variety of applications including materials measurement, tomography, and process control, including monitoring chemical and biological reactions.

Two challenges in dielectric spectroscopy are guiding and monitoring the propagation of the electric field, as the energy from the electric field must be reliably and repeatedly contained and monitored. An important consideration in designing a microwave dielectric spectroscopy technique is the frequency dependence of the measurement, and it is often important to measure the dielectric properties of a material at different frequencies or over a wide frequency range. Unfortunately, many microwave dielectric spectroscopy probes only operate over a limited frequency range.

Microwave dielectric spectroscopy probes based on a coplanar waveguide structure that relies on the proximity to or incorporation of the dielectric material being measured offer board-band operation. However, most of the electromagnetic energy is coupled into the substrate of the coplanar waveguide. This reduces the sensitivity of the measurement.

A microwave dielectric spectroscopy probe that provides broad-band performance and high sensitivity is desirable.

BRIEF SUMMARY OF THE INVENTION

A microwave spectroscopy probe has a center conductor between a first ground plane and a second ground plane. A dielectric member has fluid channel between the center conductor and the first ground plane.

DETAILED DESCRIPTION OF THE EMBODIMENTS

Figure 1A:
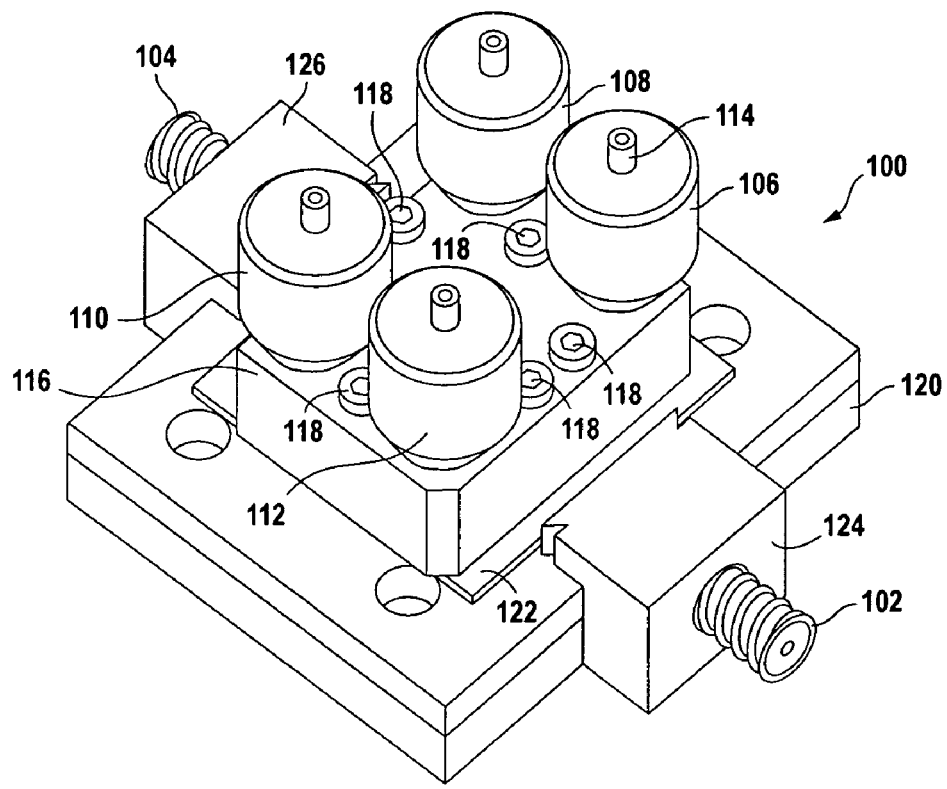
FIG. 1A shows an isometric view of a dielectric fluid microwave spectroscopy probe according to an embodiment of the invention.

A microwave dielectric spectroscopy probe for testing and measuring fluids has a channel in a dielectric portion of a slab line transmission structure. Fluids may be somewhat conductive (i.e. not purely dielectric), such as salt solutions; however, it is generally changes in the dielectric constant or dielectric loss that is being measured, as is known in the art of microwave dielectric spectroscopy. In a particular embodiment, the microwave spectroscopy probe also has a second channel in a second dielectric portion of the slab line transmission structure. The microwave spectroscopy probe includes fluid ports for providing fluid to the channel(s). The channel(s) is located between the center conductor and ground plane(s) of the slab line transmission structure.

The slab line-based microwave dielectric spectroscopy probe allows measuring the dielectric properties of fluid in the channel(s) over a wide frequency range. A wide frequency range, such as a frequency range extending above 10 GHz, and in a particular embodiment extending to at least 100 GHz, is desirable because microwave dielectric spectroscopy measurements are often empirically based. That is, one does not necessarily know where a frequency of interest (i.e. one which provides a desired indication of a material change or property) will occur. A probe providing a wide frequency range allows testing of a greater range of fluids.

The electric field in a slab line transmission structure also concentrates the electromagnetic field strength near the center conductor. This increases sensitivity by coupling the electromagnetic field into the dielectric fluid carried in the channel(s) near the center conductor. The increased sensitivity also allows dielectric spectroscopy measurements to be made on smaller sample sizes. The sample size only needs to be large enough to fill the channel(s). The probe does not need to be immersed in a vessel of fluid-under-test, as with some prior art probes.

In a particular embodiment, a slab line-based microwave dielectric spectroscopy probe is used to monitor a chemical or biological reaction in a fluid. Even though the fluid is weakly conductive, the perturbation in the transmission characteristics of the slab line transmission structure allow measurement of the fluid using a vector network analyzer ("VNA"). The probe allows measuring both reflection and transmission characteristics, which provides better accuracy of dielectric constant and loss than a conventional single-ended probes, which only allow testing reflection characteristics. The probe is also more conducive to in-line process (as opposed to batch) control because fluid can be continuously circulated through the probe during the process. The slab line-based microwave dielectric spectroscopy probe allows measurements to be made in the frequency domain, and has less dispersion, provides a truer TEM profile to the propagating wave, and has increased interaction between the fluid sample and the wave compared to conventional coplanar waveguide probes. In some embodiments, the surfaces of the channels in the probe are treated (e.g. with a protein binding agent) to react with a selected molecule (e.g. a protein), and several samples of different fluids are run through the probe until one containing the selected molecule reacts with the treated surface to provide a change in the dielectric properties of the fluid.

FIG. 1A shows a fluid microwave spectroscopy probe 100 ("probe") according to an embodiment of the invention. The probe 100 has a first RF connector 102 and a second RF connector 104 configured to be attached to coaxial cables in a high-frequency test set. For purposes of convenient discussion, and as is commonly done in the art, the term "RF" is used to describe high-frequency electrical signals, typically from about 1 MHz to about 110 GHz, even though electrical signals within this range are often also referred to as "microwave" signals. The first and second RF connectors 102, 104 allow a transmission loss measurement to be made using a VNA. Alternatively, a probe has only a single port and a return loss measurement is made. In a particular embodiment, both transmission and return loss measurements of a fluid sample are made.

Fluid ports 106, 108, 110, 112 are configured to transport fluid-under-test to and from one or more channels in a slab line transmission structure (see FIGS. 2 and 3A-3C). In a particular embodiment, a fluid port 106 includes a nipple 114 to which thin plastic tubing is attached. The fluid ports 106, 108, 110, 112 are attached to a lid 116 of the probe 100. The lid 116 is attached to a base 120 of the probe 100 with screws 118, some of which are not shown in this view. The lid 116, screws 118, and base 120 are metal, and the screws electrically connect the lid to the base. The lid and base are electrically coupled to the outer conductor of the RF connectors 102, 104 and form ground planes that act in cooperation with a slab line member 122 (see FIG. 2) to form a slab line transmission structure.

Adjustable coaxial supports 124, 126 slide up and down with respect to the base 120 to locate the center pin (see, e.g., FIG. 1B, ref num. 140) of the RF connectors 102, 104 at the proper height to electrically couple (i.e., be connected to) a center conductor (see FIGS. 1B and 2, ref. num. 142) of the slab line transmission structure. After adjusting the coaxial supports to the desired height, they are fixed with respect to the base. Adjustable coaxial supports are described in further detail in U.S. Pat. No. 6,870,448 by Whitener et al.

Figure 1B:
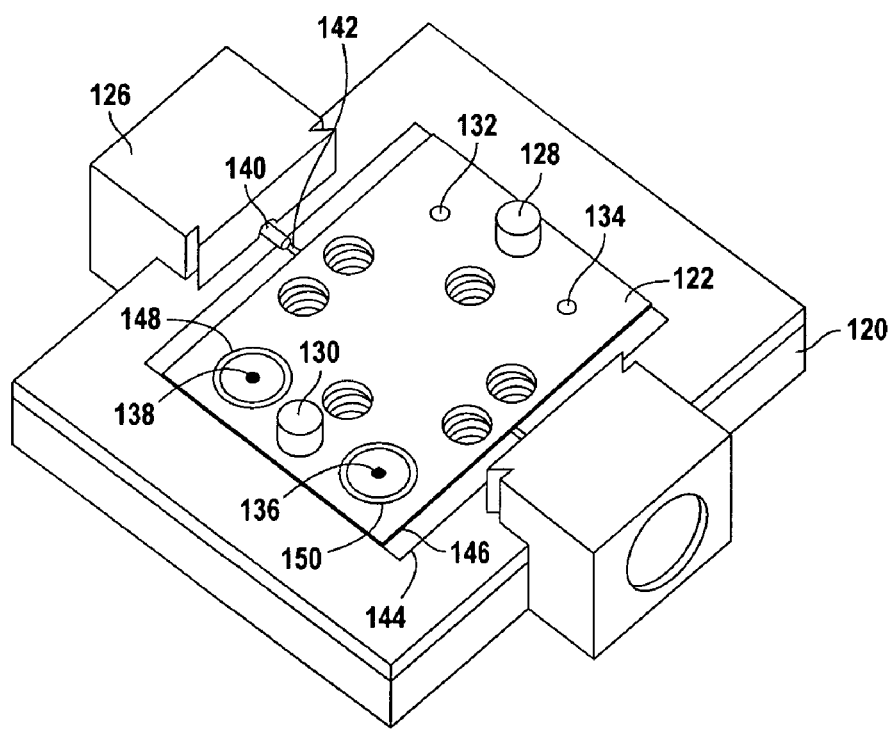
FIG. 1B is an isometric view of a portion of the dielectric fluid microwave spectroscopy probe of FIG. 1A.

FIG. 1B is an isometric view of a portion of the fluid microwave spectroscopy probe of FIG. 1A. The lid (see FIG. 1A, ref. num. 116) has been removed to expose the slab line member 122. The slab line member 122 forms a slab line transmission structure with groundplanes provided by the base 120 and lid when the probe is assembled. Guide pins 128, 130 are fixed in the base 120 and align the slab line member 122 and lid during assembly. Apertures 132, 134, 136, 138 in the slab line member 122 provide paths for fluid to be circulated through channels in the slab line member 122 (see FIG. 2 and FIGS. 3A-3C). Two apertures 132, 134 allow fluid circulation through a "top" channel (see FIG. 2, ref. num. 212), and two other apertures 136, 138 allow fluid circulation through a "bottom" channel (see FIG. 2, ref. num. 210). Alternatively, only a single channel is provided (e.g., a top channel or a bottom channel), or the top and bottom channels are fluidly coupled and a single pair of apertures allows fluid circulation through both channels.

A center pin 140 contacts a center conductor 142 of the slab line member 122. The center conductor 142 acts in cooperation with ground planes formed on either side of the slab line member 122 by the base 120 and the lid (see FIG. 1A, ref. num. 116) to form a slab line transmission line. The center pin 140 is part of a coaxial transmission structure in the adjustable coaxial support 126. The adjustable coaxial support allows the center pin 140 to be brought into contact with the center conductor 142, allowing for variations in the height of the top of the center conductor 142 (e.g., for variations, either selected or as a result of manufacturing tolerances, in the thickness of the dielectric member 144).

The center conductor 142 is between a first dielectric member 144 and a second dielectric member 146 of the slab line member 122. The first dielectric member is a generally planar structure of dielectric material that includes a channel extending above a portion of the center conductor 142. In a particular embodiment, the first dielectric member 144 is a first stack of polyimide sheets and the second dielectric member 146 is a second stack of polyimide sheets. Holes 148, 150 in the second dielectric member 146 allows access to the apertures 136, 138 in the first dielectric member 144 to couple fluid to the bottom channel (see FIG. 2, ref. num. 210) in the first dielectric member 144. In a particular embodiment, O-rings are used on the ends of the fluid ports (see FIG. 1A, ref. nums. 106, 108, 110, 112), which are pressed against the second dielectric member 146 and against the first dielectric member 144, respectively, when the lid (see FIG. 1A, ref. num. 116) is secured to the base 120. Alternatively, fluid is coupled to one or more channels in the slab line member 122 through the base 120 or side(s) of the slab line member.

Figure 2:
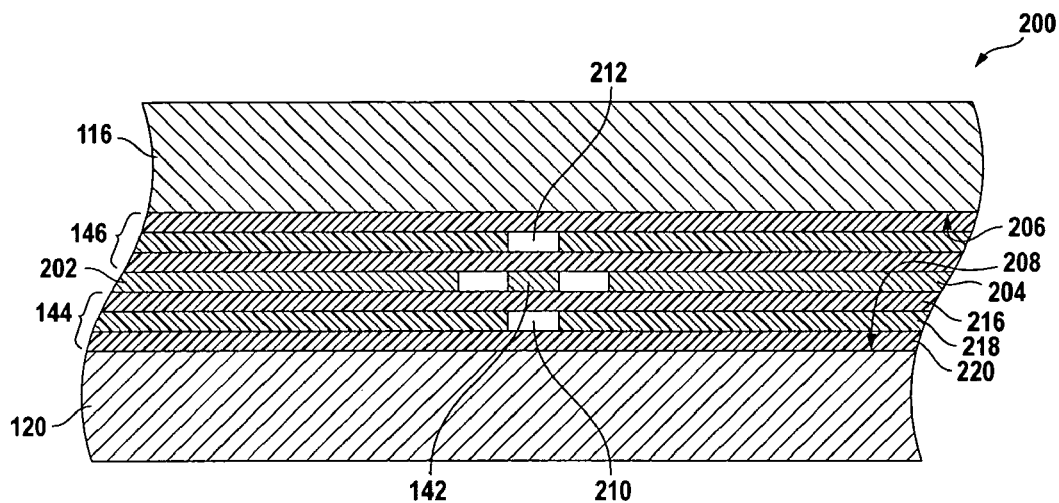
FIG. 2 shows a cross section of a portion of a dielectric fluid microwave spectroscopy probe according to an embodiment of an invention.

FIG. 2 shows a cross section of a portion of a fluid microwave spectroscopy probe 200 according to an embodiment of an invention. The center conductor 142 is "sandwiched" between the first dielectric member 144 and the second dielectric member 146. In a particular embodiment, the center conductor 142 is formed from beryllium-copper sheet about fifty microns thick by electronic-discharge machining ("EDM"), and is about one-hundred and ninety microns wide. Shims 202, 204 are made from the same sheet stock and are set-back a sufficient distance from the center conductor 142 to not substantially couple electromagnetic energy from the center conductor 142. In a particular embodiment, the shims 202, 204 are electrically floating. Alternatively, the shims are made of other material(s), such as polyimide sheet.

The electromagnetic energy is concentrated above and below the center conductor 142, i.e., between the center conductor and the ground planes 206, 208 formed by the lid 116 and base 120 of the probe. Fluid channels 210, 212 in the first dielectric member 144 and in the second dielectric member 146 are positioned between the center conductor 142 and ground planes 206, 208 of the slab line transmission structure of the probe 200. The fluid channels 210, 212 are located in regions where electromagnetic field lines are concentrated in the slab line, improving the coupling of electromagnetic energy to fluid carried in the fluid channels 210, 212 and thus improving sensitivity of microwave spectroscopy measurements.

In a particular embodiment, the first dielectric member 144 is made from three sheets 216, 218, 220 of polyimide, each sheet being about seventy-five microns thick. The fluid channel 210 is fabricated in the middle sheet 218 of polymide. Side channels (see, e.g., FIG. 3A, ref. nums.302, 304) are also fabricated in the middle sheet to couple fluid to and from the fluid channel 210. Fluid vias (not shown) are fabricated in the upper sheet 216, and access holes (see FIG. 1B, ref. nums. 148, 150) are fabricated in the shim 204 and in the upper dielectric member 146.

Alternatively, the slab line member is made using photolithographic techniques, such as printed circuit board ("PCB") techniques, but has the same general configuration of a fluid channel disposed between the center conductor and a ground plane of a slab line transmission structure. In the embodiment of FIG. 2, the fluid channels 210, 212 have a width about the same as the center conductor 142, which in a particular embodiment is about one-hundred and ninety microns. Alternatively, the channels are wider or narrower than the center conductor, or the channels have different widths. In yet another embodiment, a slab line member has a single fluid channel above or below the center conductor. Providing two fluid channels and providing a fluid-under-test to both fluid channels provides greater sensitivity when performing microwave spectroscopy measurements.

Figure 3A:
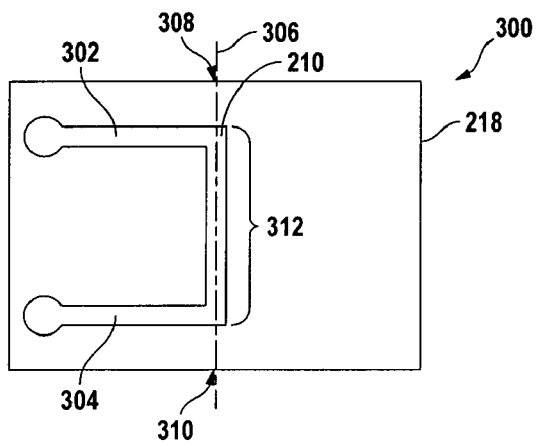
FIG. 3A shows a plan view of a slab line dielectric layer according to an embodiment of the invention.

FIG. 3A shows a plan view of a slab line dielectric layer 300 according to an embodiment of the invention. The slab line dielectric layer 300 is the middle layer 218 of a stack of polyimide layers in a dielectric member 144, for example. Side channels 302, 304 provide and remove fluid from the fluid channel 210. The center conductor (see FIGS. 1B and 2, ref. num. 142) extends along the line 306 from a first edge 308 to a second edge 310 of the slab line dielectric layer 300. The fluid channel 210 extends along the line 306 for a portion 312 of the distance between the first edge 308 and the second edge 310. Generally, the greater the portion of the distance that the fluid channel overlies or underlies the center conductor, the better the sensitivity of microwave spectroscopy measurements.

Figure 3B:
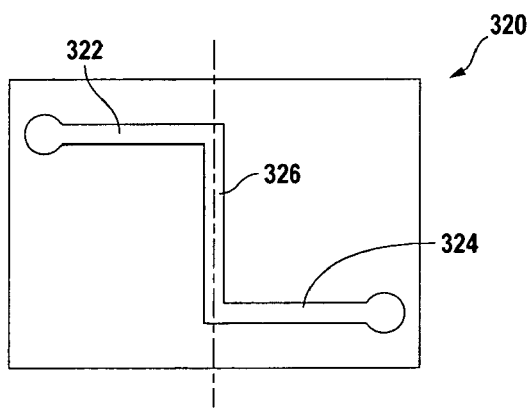
FIG. 3B shows a plan view of a slab line dielectric layer according to another embodiment of the invention.

FIG. 3B shows a plan view of a slab line dielectric layer 320 according to another embodiment of the invention. Side channels 322, 324 provide and remove fluid from the fluid channel 326 from opposite sides.

Figure 3C:
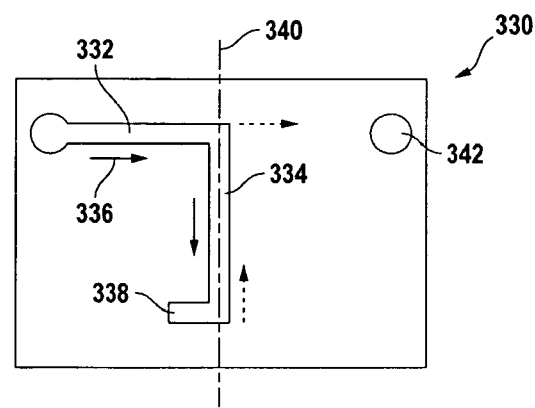
FIG. 3C shows a plan view of a slab line dielectric layer according to another embodiment of the invention.

FIG. 3C shows a plan view of a slab line dielectric layer 330 according to another embodiment of the invention. A first side channel 332 provides fluid to a first fluid channel 334, as indicated by the arrow 336. A fluid via 338 couples the fluid-under-test from the first fluid channel 334 to a second fluid channel (not shown, see, e.g., FIG. 2, ref. nums. 210, 212) beneath the first fluid channel and beneath the center conductor (also not shown) of a slab line in a microwave spectroscopy probe. The center conductor runs along the line 340, as discussed above with reference to FIG. 3A, numeral 306. A second side channel (not shown) in a lower dielectric member couples fluid from the second fluid channel to an outlet 342. Thus, fluid-under-test can be circulated through both the first and second fluid channels using only two fluid ports on the probe. This not only simplifies setting up the measurements, but also insures that the flow through the first fluid channel is equal to the flow through the second fluid channel.

Figure 4A:
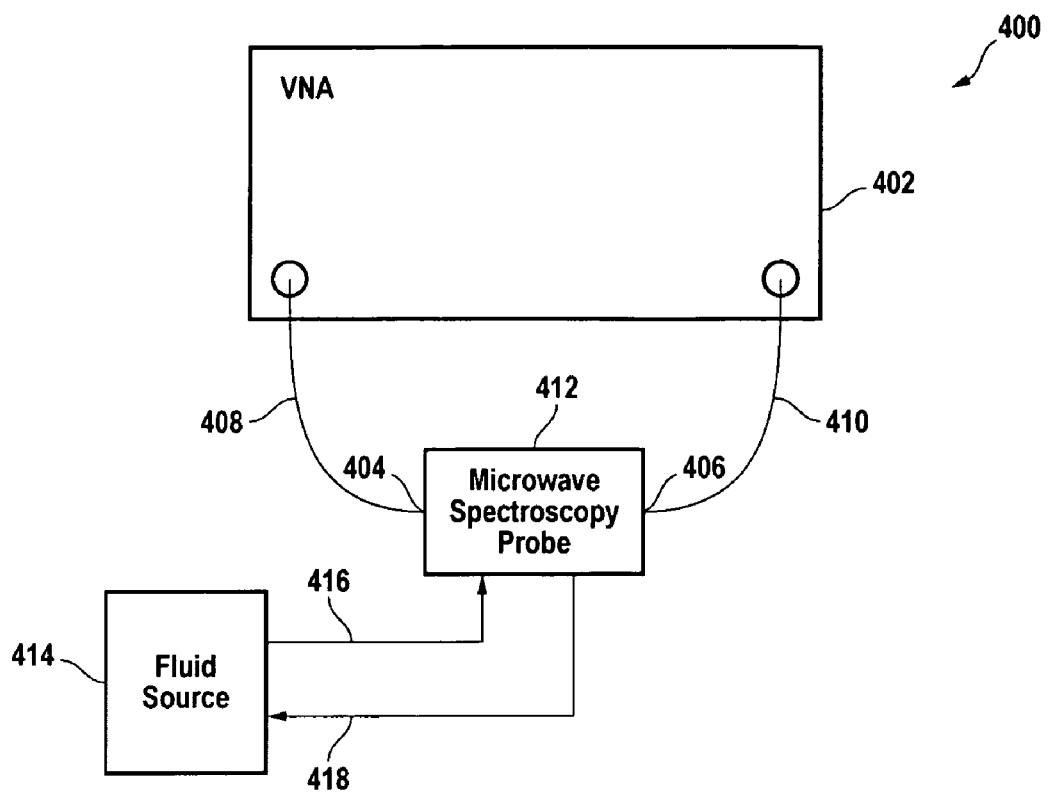
FIG. 4A shows a microwave spectroscopy test system according to an embodiment of the invention.

FIG. 4A shows a microwave spectroscopy test system 400 according to an embodiment of the invention. A vector network analyzer ("VNA") 402 is connected to the RF ports 404, 406 (see, e.g., RF connectors 102, 104 in FIG. 1A) with microwave test cables 408, 410. A transmission measurement (e.g., $S_{21}$ or transmission loss) is made using the VNA 402. Generally, a first transmission loss is measured with the VNA 402 without fluid being supplied to the microwave spectroscopy probe 412, and then a second transmission loss is measured with the VNA 402 with fluid being supplied to a fluid channel in a dielectric member of a slab line transmission structure in the probe 412. In a particular embodiment, fluid is also simultaneously supplied to a second fluid channel in a second dielectric member of the slab line transmission structure.

Fluid is supplied by, and returned to, a fluid source 414 through fluid conduits 416, 418, such as plastic tubing. Alternatively, the fluid-under-test is not returned to the fluid source 414. In one embodiment, the fluid is static (i.e., not moving) in the probe 412 during the transmission loss measurement. In another embodiment, the fluid is being pumped through the probe during measurement, and in a particular embodiment, the transmission loss is being continuously measured as the fluid is pumped through the probe 412 to monitor a reaction, such as a chemical or biological reaction, occurring in the fluid. In a particular example, microwave spectroscopy of the fluid flowing through the probe is used to control a process operating on the fluid. In some embodiments, transmission loss is measured at several different frequencies. The slab line transmission structure in the probe provides broad-band response for measuring a fluid over a wide range of frequencies, or alternatively, measuring various fluids at different frequencies.

Figure 4B:
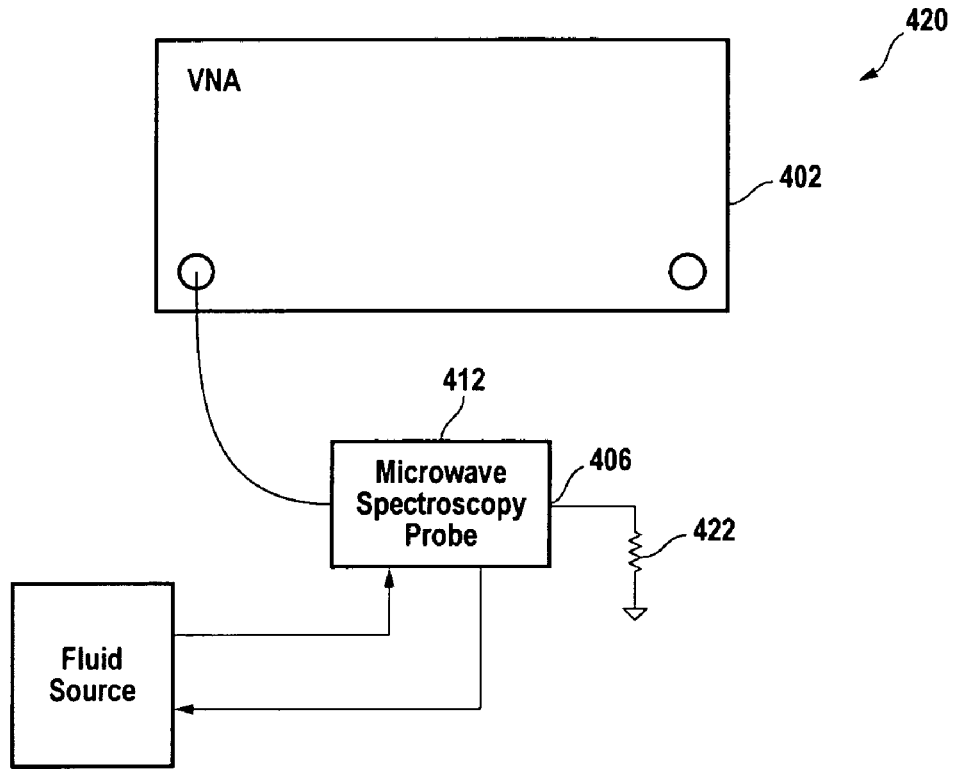
FIG. 4B shows a microwave spectroscopy test system according to another embodiment of the invention.

FIG. 4B shows a microwave spectroscopy test system 420 according to another embodiment of the invention. A termination 422 [Short? Open? Load?] is coupled to an RF port 406 of the probe 412. The VNA 402 performs a return loss measurement (e.g., $S_{11}$) on the probe, typically comparing the return loss of the probe without fluid to the return loss with fluid. The two RF ports of the probe allow the user to attach a short, an open, or a load to one port while measuring the other port, providing additional data (compared to a single-port probe). Alternatively a termination is incorporated into a probe. The ability to make a one-port measurement is desirable because it allows using a test instrument having a single port, which is potentially less costly than a two-port test instrument.

While the preferred embodiments of the present invention have been illustrated in detail, it should be apparent that modifications and adaptations to these embodiments might occur to one skilled in the art without departing from the scope of the present invention as set forth in the following claims.

What is claimed is:

1. A microwave spectroscopy probe comprising:
    a first ground plane;
    a second ground plane;
    a center conductor disposed between the first ground plane and the second ground plane, said center conductor comprising a planar strip characterized by a thickness;
    a first dielectric member having a first fluid channel disposed between the center conductor and the first ground plane;
    a second dielectric member disposed between the center conductor and the second ground plane; and
    shims disposed between the first dielectric member and the second dielectric member, said shims being co-planar with said center conductor and having a thickness substantially equal to said thickness of said center conductor.

2. The microwave spectroscopy probe of claim 1 further comprising a second fluid channel in the second dielectric member disposed between the center conductor and the second ground plane.

3. The microwave spectroscopy probe of claim 2 wherein the first fluid channel is fluidly coupled to the second fluid channel.

4. The microwave spectroscopy probe of claim 1 further comprising a first fluid port fluidly coupled to the first fluid channel and a second fluid port fluidly coupled to the first fluid channel.

5. The microwave spectroscopy probe of claim 1 wherein the center conductor, first dielectric member, second dielectric member, first ground plane and second ground plane cooperate to form a slab line transmission structure.

6. The microwave spectroscopy probe of claim 1 further comprising
a first RF connector electrically coupled to the first ground plane, the second ground plane, and the center conductor, and
a second RF connector electrically coupled to the first ground plane, the second ground plane, and the center conductor.

7. The microwave spectroscopy probe of claim 1 wherein the first dielectric member is disposed between the center conductor and the first ground plane, the first dielectric member having a first fluid channel disposed between the center conductor and the first ground plane.

8. The microwave spectroscopy probe of claim 1 wherein a width of the first fluid channel is less than 200 microns.

9. A microwave spectroscopy probe comprising:
a first ground plane;
a second ground plane;
a center conductor disposed between the first ground plane and the second ground plane;
a first dielectric member having a first fluid channel disposed between the center conductor and the first ground plane;
a second dielectric member disposed between the center conductor and the second ground plane; and
shims disposed between the first dielectric member and the second dielectric member;
wherein the first dielectric member comprises three dielectric sheets, the first fluid channel being formed in a middle dielectric sheet.

10. The microwave spectroscopy probe of claim 9 further comprising a first side channel fluidly coupled to the first fluid channel and a second side channel fluidly coupled to the first fluid channel; wherein said first side channel and said second side channel are oriented along directions that are substantially orthogonal to the direction along which said first fluid channel is oriented.

11. A microwave spectroscopy probe comprising:
a first ground plane;
a second ground plane;
a center conductor disposed between the first ground plane and the second ground plane;
a first dielectric member having a first fluid channel disposed between the center conductor and the first ground plane;
a second dielectric member disposed between the center conductor and the second ground plane; shims disposed between the first dielectric member and the second dielectric member;
a first RF connector electrically coupled to the first ground plane, the second ground plane, and the center conductor; and
a second RF connector electrically coupled to the first ground plane, the second ground plane, and the center conductor; wherein the first RF connector is a first coaxial connector, the second RF connector is a second coaxial connector, and the first dielectric member, the center conductor, and the second dielectric member form a slab line member and further comprising
a base supporting the slab line member;
a first adjustable coaxial support slidably coupled to the base so as to allow adjustment of the first coaxial connector with respect to the center conductor of the slab line member; and
a second adjustable coaxial support slidably coupled to the base so as to allow adjustment of the second coaxial connector with respect to the center conductor of the slab line member.

12. A microwave spectroscopy probe comprising:
a first ground plane;
a second ground plane;
a center conductor disposed between the first ground plane and the second ground plane, wherein the center conductor is characterized by a thickness, a width and a length, the length being substantially greater than the thickness and the width;
a first dielectric member having a first fluid channel disposed between the center conductor and the first ground plane;
a second dielectric member disposed between the center conductor and the second ground plane; and
shims disposed between the first dielectric member and the second dielectric member;
wherein the first fluid channel extends along the length of the center conductor above or below the center conductor so as to channel fluid between the center conductor and the first ground plane along the length of the center conductor.

13. A microwave spectroscopy probe comprising:
a first ground plane;
a second ground plane;
a center conductor disposed between the first ground plane and the second ground plane;
a first dielectric member having a first fluid channel disposed between the center conductor and the first ground plane;
a second dielectric member disposed between the center conductor and the second ground plane; and
shims disposed between the first dielectric member and the second dielectric member;
wherein the shims are made from the same sheet stock as the center conductor and are arranged a sufficient distance away from the center conductor so as to not substantially couple electromagnetic energy from the center conductor.

14. The microwave spectroscopy probe of claim 13 wherein the shims are electrically floating.

* * * * *